(12) United States Patent
Singhal (10) Patent No.: US 11,207,471 B2
(45) Date of Patent: Dec. 28, 2021

(54) APPARATUS AND METHOD FOR AN INTEGRATED REUSEABLE INJECTION DEVICE WITH A MEDICINE VIAL FOR HOME USERS

(71) Applicant: Tara Chand Singhal, Torrance, CA (US)

(72) Inventor: Tara Chand Singhal, Torrance, CA (US)

(*) Notice: Subject to any disclaimer, the term of this patent is extended or adjusted under 35 U.S.C. 154(b) by 0 days.

(21) Appl. No.: 14/014,717

(22) Filed: Aug. 30, 2013

(65) Prior Publication Data

US 2015/0065990 A1  Mar. 5, 2015
US 2016/0228655 A9  Aug. 11, 2016

Related U.S. Application Data

(63) Continuation-in-part of application No. 12/807,481, filed on Sep. 7, 2010.

(60) Provisional application No. 61/711,179, filed on Oct. 8, 2012.

(51) Int. Cl.
| | |
|---|---|
| *A61M 5/32* | (2006.01) |
| *A61M 5/315* | (2006.01) |
| *A61M 5/28* | (2006.01) |
| *A61M 5/31* | (2006.01) |
| *A61M 5/00* | (2006.01) |

(52) U.S. Cl.
CPC .......... *A61M 5/3298* (2013.01); *A61M 5/288* (2013.01); *A61M 5/31511* (2013.01); *A61M 5/001* (2013.01); *A61M 5/3129* (2013.01); *A61M 5/3202* (2013.01); *A61M 2005/3125* (2013.01); *A61M 2005/31518* (2013.01)

(58) Field of Classification Search
CPC .. A61M 5/001; A61M 5/3202; A61M 5/3213; A61M 5/347; A61M 5/3293; A61M 2005/314; A61M 2005/3142; A61M 2205/0205; A61M 2205/0222; A61M 5/50; A61M 5/3204
USPC ....... 604/199, 192, 188, 403, 506, 171, 172; 206/365
See application file for complete search history.

(56) References Cited

U.S. PATENT DOCUMENTS

| | | | | |
|---|---|---|---|---|
| 2,400,722 A | * | 5/1946 | Swan | 206/210 |
| 2,616,420 A | * | 11/1952 | Hart | C01C 1/248 |
| | | | | 604/193 |
| 2,828,742 A | * | 4/1958 | Ashkenaz | A61M 5/288 |
| | | | | 604/193 |
| 3,090,383 A | * | 5/1963 | Brooks | 604/236 |
| 3,192,925 A | * | 7/1965 | Cunningham | A61M 5/282 |
| | | | | 600/577 |
| 3,354,881 A | * | 11/1967 | Bloch | 604/198 |

(Continued)

*Primary Examiner* — Brandy S Lee
*Assistant Examiner* — Hong-Van N Trinh
(74) *Attorney, Agent, or Firm* — Davidson Berquist Jackson & Gowdey LLP (57) ABSTRACT

A portable handheld fluid-medicine-injection device for individual users, has a medicine vial has a substantially rectangular cross section that reduces a thickness profile of the device and a dispense mechanism coupled with the vial, the dispense mechanism has an inject push rod inside a threaded cylinder that reduces a length profile of the device. The device has a needle with a needle mount/dismount mechanism coupled with the medicine vial and a needle storage mechanism that stores the needle when not in use and replenishes the needle for reuse.

17 Claims, 11 Drawing Sheets

(56) References Cited

U.S. PATENT DOCUMENTS

| | | | |
|---|---|---|---|
| 3,413,974 A * | 12/1968 | Cohen | A61M 5/34 604/201 |
| 4,178,930 A * | 12/1979 | Fisher, Jr. | A61M 5/34 604/192 |
| 4,303,069 A * | 12/1981 | Cohen | A61M 5/288 604/192 |
| 4,416,663 A * | 11/1983 | Hall | 604/198 |
| 4,758,230 A * | 7/1988 | Rycroft | A61M 5/282 206/366 |
| 4,915,697 A * | 4/1990 | DuPont | A61M 5/326 604/192 |
| 5,190,521 A * | 3/1993 | Hubbard | A61M 5/422 604/117 |
| 5,286,258 A * | 2/1994 | Haber et al. | 604/90 |
| 5,370,621 A * | 12/1994 | Godat et al. | 604/199 |
| 5,505,694 A * | 4/1996 | Hubbard | A61M 5/282 604/242 |
| 5,707,365 A * | 1/1998 | Haber et al. | 604/191 |
| 5,876,380 A * | 3/1999 | Manganini | A61M 5/001 604/191 |
| 6,530,904 B1 * | 3/2003 | Edwards et al. | 604/197 |
| 7,247,151 B2 * | 7/2007 | Slawson | 604/197 |
| 8,639,288 B1 * | 1/2014 | Friedman | 455/556.1 |
| 2003/0139706 A1 * | 7/2003 | Gray | 604/199 |
| 2003/0187401 A1 * | 10/2003 | Doyle | A61M 5/3243 604/198 |
| 2005/0165362 A1 * | 7/2005 | Slawson | 604/197 |
| 2005/0171477 A1 * | 8/2005 | Rubin et al. | 604/156 |
| 2005/0215955 A1 * | 9/2005 | Slawson | 604/192 |
| 2006/0184117 A1 * | 8/2006 | Knight | A61M 5/24 604/135 |
| 2006/0247579 A1 * | 11/2006 | Friedman | 604/197 |
| 2009/0082727 A1 * | 3/2009 | Moeller et al. | 604/132 |
| 2011/0071393 A1 * | 3/2011 | Liu et al. | 600/432 |
| 2012/0029469 A1 * | 2/2012 | Horvath | A61M 5/32 604/506 |
| 2014/0114247 A1 * | 4/2014 | Karlsson et al. | 604/135 |

* cited by examiner

At step 100, having a medicine vial with a substantially rectangular cross section for reducing a thickness profile of the device and having a dispense mechanism coupled with the vial, the dispense mechanism having an inject push rod inside a threaded cylinder for reducing a length profile of the device.

At step 102, having a needle with a needle mount/dismount mechanism coupling the mechanism with the medicine vial and having a needle storage mechanism for storing the needle when not in use and replenishing the needle for reuse.

At step 104, integrating the vial, the dispense mechanism, the needle, the mount/dismount mechanism and the needle storage mechanism into a single device enabling a use of the device for injecting medicine without a separate supply of single use injection needles.

At step 106, integrating the vial, the dispense mechanism, the needle, the mount/dismount mechanism and the needle storage mechanism into a single device with the length profile and the thickness profile of the device to be carried in a clothing pocket.

At step 108, having the device profile substantially 3/8" thick, 3/4" wide and 4 ½ inches long.

FIGURE 10

APPARATUS AND METHOD FOR AN INTEGRATED REUSEABLE INJECTION DEVICE WITH A MEDICINE VIAL FOR HOME USERS

CROSS REFERENCE

This application claims priority from Provisional Application Ser. No. 61/711,179, filed on Oct. 8, 2012 of Tara Chand Singhal, for Apparatus and Method for an Integrated Medicine Vial and Injection Device for Individual Use. The contents of application No. 61/711,179 are incorporated herein by reference.

This application is also related to and claims priority from application Ser. No. 12/807,481 filed on Sep. 7, 2010 of Tara Chand Singhal for Apparatus and methods for reuse of injection needle for home users.

FIELD OF THE INVENTION

An integrated portable handheld fluid-medicine-injection device for home users is described. The device integrates a medicine vial, a dispense mechanism coupled with the vial, a needle with a needle mount/dismount mechanism coupled with the medicine vial and a needle storage mechanism that stores the needle when not in use and replenishes the needle for reuse.

BACKGROUND

People across the United States and around the world suffer from a metabolic disease called diabetes. For many of these people who suffer from diabetes, taking insulin by injection is a requirement. There are two forms of insulin. One is longer acting insulin and is preferably injected once a day. The other type of insulin is faster acting insulin and is injected multiple times a day based on meal plans.

Industry provides two different methods of injecting insulin; one is via a syringe and a bottle of insulin. The syringe is used to draw a required amount of insulin from the bottle and then used to inject. This method is mostly used for the slow acting insulin.

The other method of injecting insulin is via what the industry calls an insulin pen, where a pen like device has a medicine vial coupled with an inject mechanism. Many different companies make such insulin pens. One example is Qwik® pen from Lily®.

These insulin pens given their form-factor are considered and believed to be convenient to carry in a person's personal possession and used through out the day by users. The users of these insulin pens need to carry a separate supply of single use short needles. These needles are taken out of their storage container and mounted on the medicine vial of the insulin and these needles, once used, are removed from the vial and discarded.

It is the objective of the embodiments herein to improve on the form-factor of the insulin pens and integrate the needle on the medicine vial without having to carry a separate supply and a container of single use needles. It is also the objective to reduce the number of steps a user would have to perform and also to reduce the overall size of such an integrated insulin pens to make it easier to carry and use such insulin pens.

SUMMARY

A portable handheld fluid-medicine-injection device for home users is described. Such a device is used for and useful for injecting insulin and may be used for and useful for injecting other fluid-medicines for home use.

The device has a needle with a needle mount/dismount mechanism coupled with the medicine vial and a needle storage mechanism that stores the needle in a needle storage medium when the needle is not in use and replenishes the needle for reuse. The art of needle storage medium has been described in a prior application of the inventor, Ser. No. 12/807,481 filed on Sep. 7, 2010.

The vial, the dispense mechanism, the needle, the needle mount/dismount mechanism and the needle storage mechanism are integrated into a single device that enables the use of the device for injecting medicine without a separate supply of single use injection needles.

The vial, the dispense mechanism, the needle, the mount/dismount mechanism and the needle storage mechanism are integrated into a single device with the length profile and the thickness profile of the device to be carried in a clothing pocket.

The device has a substantially rectangular cross section including the medicine vial and a dispense mechanism coupled with the vial. Such a cross-section reduces the thickness profile of the device The device preferably has a profile with substantially ⅜" thick, ¾" wide and 4½ inches long making it easy to carry and use. This profile is in contrast to the prior art such pen devices which are generally 5½ inches long and ⅝" inches in diameter. The dispense mechanism has an inject push rod inside a threaded cylinder that reduces a length profile of the device.

These and other aspects of the embodiments herein are further described in detail with the help of the accompanying drawings and the description, where similar numbers are used to identify the features of the embodiments.

BRIEF DESCRIPTION OF THE DRAWINGS

Some of the novel features of the embodiments will be best understood from the accompanying drawings, taken in conjunction with the accompanying description, in which similar reference characters refer to similar parts, and in which.

DESCRIPTION

Introduction

Figure 1:
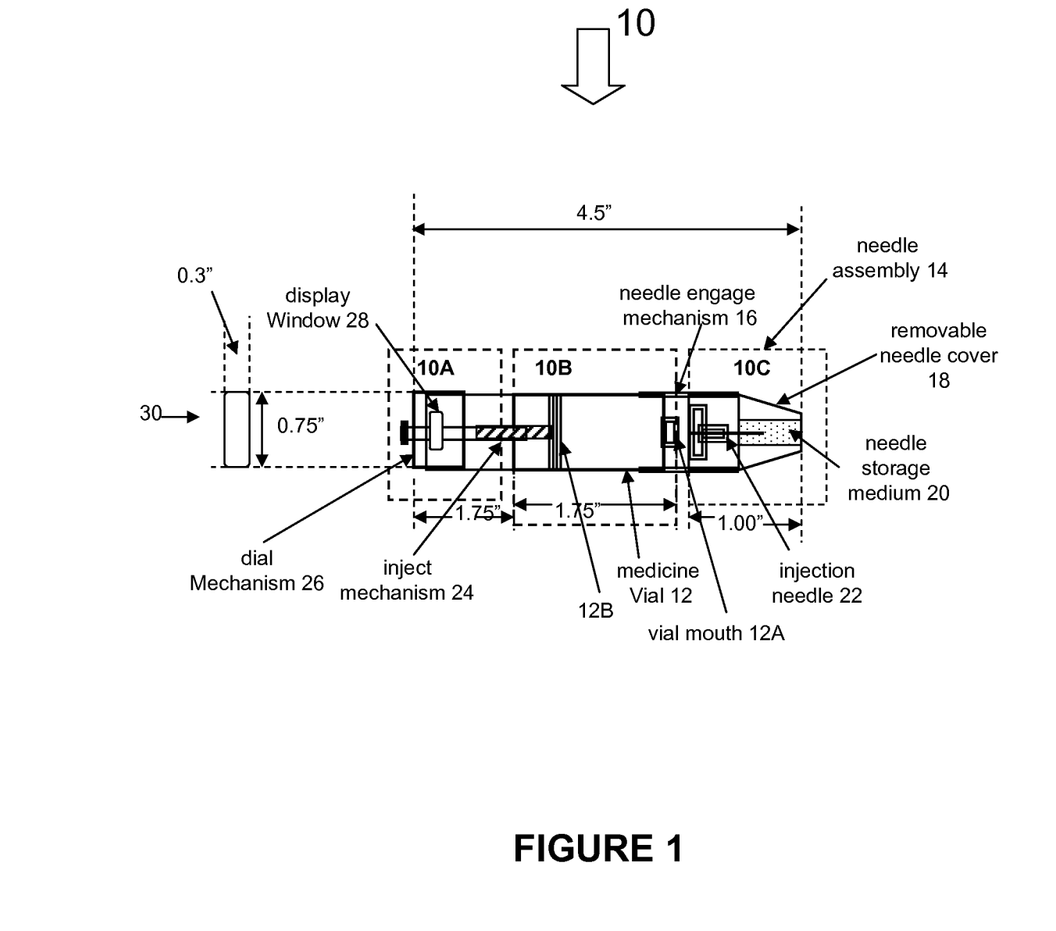
FIG. 1 shows a block diagram that illustrates features of the preferred embodiment of an integrated medicine-injection device for home users.

With reference to FIG. 1, an integrated insulin injection device 10 is described. No limitation is intended for the type of medicinal fluid that may be injected, even though insulin is the preferred medicinal fluid.

As illustrated in FIG. 1, the device 10 has three sub-assemblies 10A, 10B and 10C.

The sub-assembly 10A is an inject sub-assembly and provides for an inject mechanism 24, a dial mechanism 26 and a inject quantity display window 28.

The sub-assembly 10B has a medicine vial 12 with a vial mouth 12A and a inject push piston 12B, and a needle engagement mechanism 16.

The sub-assembly 100 is a needle assembly and provides for an injection needle 22, and a needle storage medium 20 that is positioned inside a removable needle cover 18.

The three sub-assemblies 10A, 10B and 100 of the device 10 are integrated into a single assembled device 10 making its easier to carry and use. The device 10 would be carried in the personal possession of a user as injecting insulin is performed multiple times in a day that is tied to consumption of food and or blood glucose readings and may be required to be performed away from home and on the move.

Prior art may teach or suggest some aspects of sub-assembly 10A and sub-assembly 10B. A prior pending application of the inventor Ser. No. 12/807,481 may teach or suggest sub-assembly 100. Therefore, what is believed are unique features of the instant device 10 are summarized here.

The device 10 has a length profile that is substantially 4.5" in length and a thickness profile that is substantially 3/8" thick and a width profile that is substantially 3/4" wide. These are notional dimensions and may be different than these dimensions without departing from the spirit and scope of the invention.

This profile makes it convenient to carry the device 10 in pocket and personal possession of a user. In contrast, prior art insulin pen devices that generally have a length of 5½ inches and a diameter of 5/8".

Prior art device has a medicine vial capacity of 300 units. The device 10 also has a similar capacity and preferably has a capacity of around 200 units.

Like prior art device, medicine in device 10 also requires refrigeration when the vial has not begun to be used to maintain the medicine potency during storage. It is believed, a medicine capacity of 200 units in device 10 helps reduce the use period and it is believed may be better able to maintain potency during a use period of about two weeks.

Further the device 10 in the sub-assembly 100 integrates a re-useable injection needle and a needle-mount and needle-dismount mechanism to and from the medicine vial as part of the device 10. This obviates the need or necessity to carry a separate supply of injection needles and manually mount and dismount such injection needles. The needle mount/dismount mechanism is integrated with the medicine vial.

Further this feature of re-useable injection needle also alleviates the issue of having to discard each needle after each use as in prior art insulin pen devices. Therefore, it is believed for these reasons the device 10 would be preferred by the insulin pen users in contrast to the prior art insulin pens.

While the sub-assembly 10C has been described as integrated with or useable with certain preferred versions or sizes of sub-assembly 10B and 10A, it should be understood that no limitation is placed or intended to be placed on the sub-assembly 100 and its use with other versions of sub-assembly 10A and 10B. That is, in the spirit and scope of the invention, sub-assembly 100 may be used, integrated or assembled with other sizes and types of medicine vials and inject mechanisms.

The sub-assembly 10A and its mechanism are described with the help of FIGS. 3, 4, 5A, and 5B. The sub-assembly 10B and its mechanisms are described with the help of FIGS. 2 and 6. The sub-assembly 100 and its mechanism are described with the help of FIGS. 7, 8 and 9. FIG. 10 provides a method diagram for device 10.

These and other aspects of the preferred embodiments of device 10 are described in detail herein where the headings are provided for reader convenience. For ease in understanding the embodiments, details of sub-assembly 10B are described first before the details of sub-assembly 10A.

Sub-Assembly Medicine Vial 10B

Figure 2:
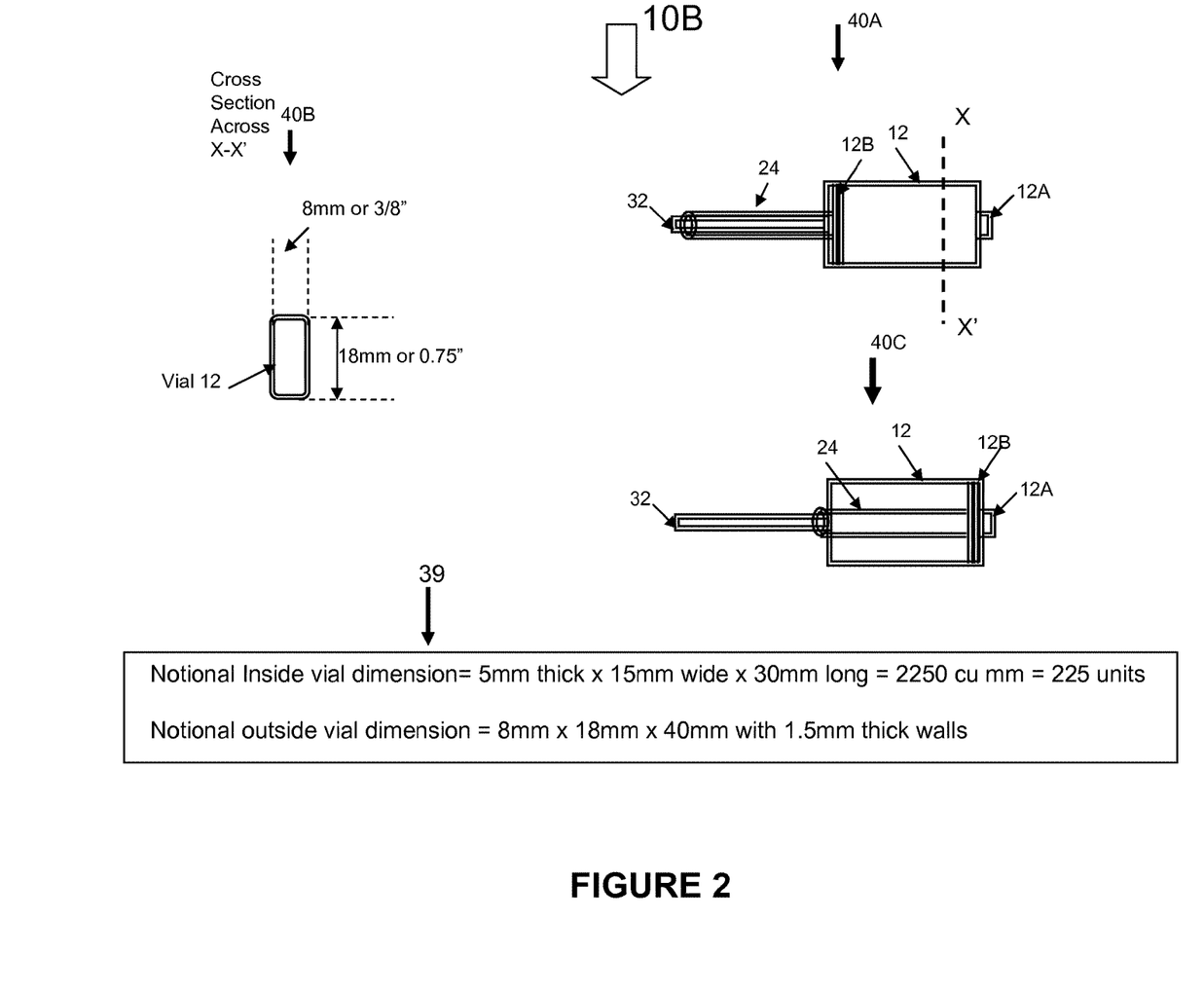
FIG. 2 is a block diagram that illustrates features of a medicine vial and its profile of a preferred embodiment of an integrated medicine-injection device for individual use.

FIG. 2 illustrates in view 40A, a medicine vial 12 that has a vial mouth 12A and a push member 12B. The push member 12B is coupled with a cylindrical tube 24 with internal threads. A rod 32 is positioned and screwed inside the tube 24 as has been illustrated later in the inject sub-assembly 10A.

View 40B illustrates a cross section of the vial along X-X'. The cross section 40B illustrates that the shape of the vial is rectangular with substantially 3/4" width and 3/8" thickness. Like the vial 12 rest of the device 10 parts 10A and 100 also have substantially the same profile in width and in thickness of the device 10.

This profile is preferred as opposed to prior art profiles of round shape medicine vials to reduce the thickness profile for making it easier to carry the device 10 in a shirt pocket.

View 40C shows the vial 12 when the push member 12B has been pushed to a position inside the vial 12 to have used all the medicine in the vial. In this view the cylinder 24 has moved inside the vial when the rod 32 has been unscrewed from the cylinder 24 and thus the rod 32 remains outside the vial 12.

View 39 shows some typical dimensions of the vial and its inside and outside dimensions with a view to illustrate a storage volume of this type of profile vial. With an inside vial size of 5 mm thick, 15 mm wide and 30 mm long the storage capacity of the vial is 2250 Cubic mm or 225 units, where a 1 ml has 100 units. These are notional dimensions and may be a little smaller or larger then these to provide a storage capacity of any where from 2 ml to 3 ml or 200 units to 300 units of medicine. Prior art storage capacity for insulin pens is 3 ml or 300 units.

Figure 6:
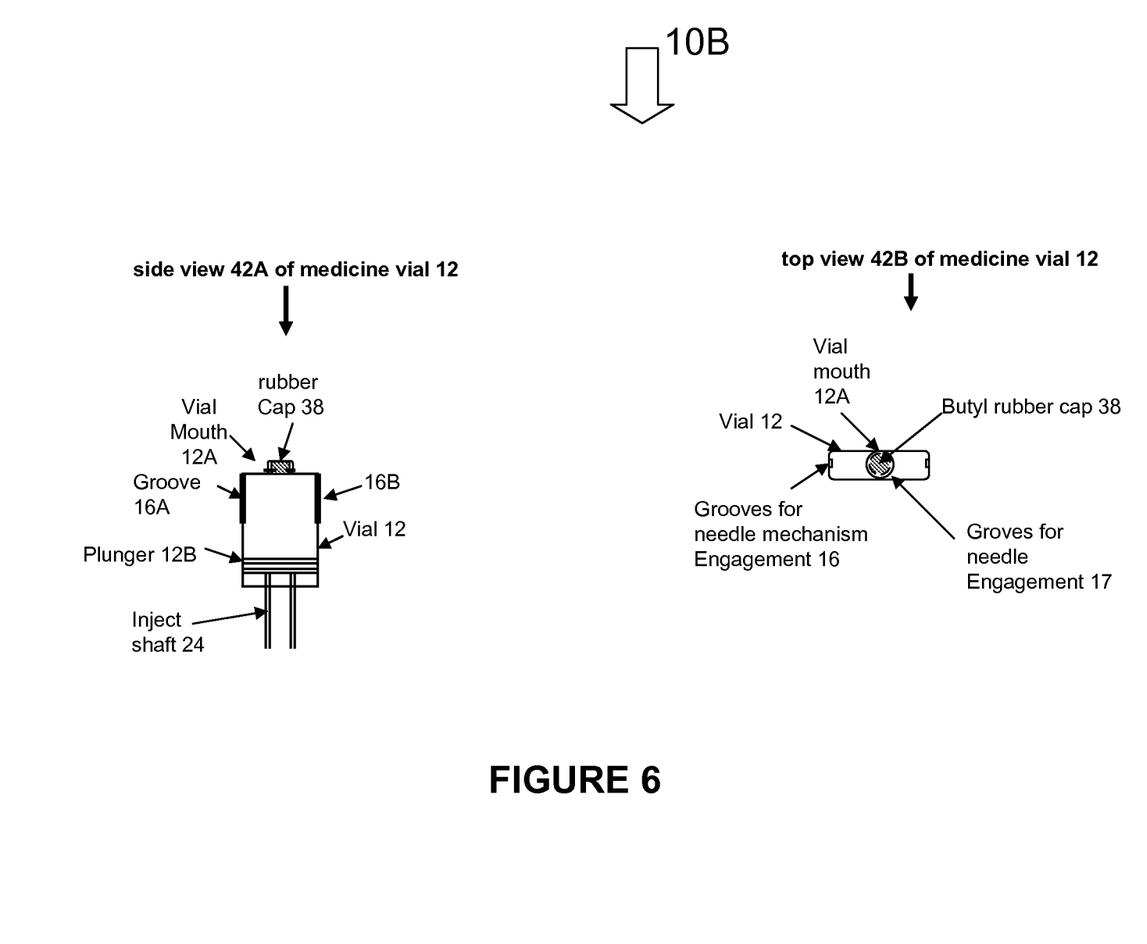
FIG. 6 is block diagrams that illustrates features of a medicine vial of a preferred embodiment of an integrated medicine-injection device for individual use.
Figure 7:
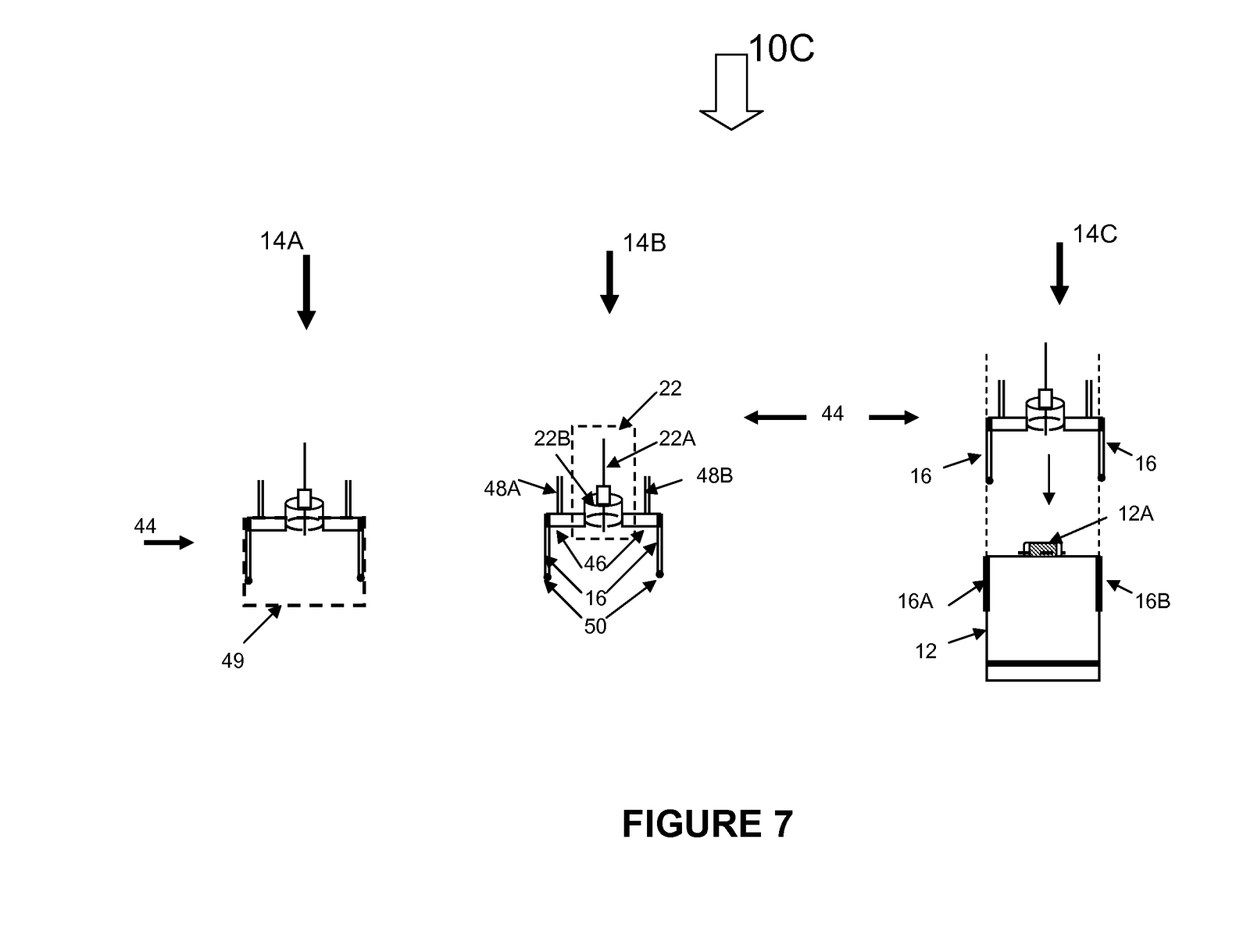
FIG. 7 are block diagrams that illustrates features of an injection needle and its associated mechanism for mounting on a medicine vial of a preferred embodiment of an integrated medicine-injection device for individual use.

FIG. 6 illustrates a side view 42A of the vial 12. The vial mouth 12A has a rubber cap 38. The sides of the vial 12 have groves 16A and 16B for use with a needle engagement mechanism 16 as illustrated later with reference to FIGS. 7A and 7B. FIG. 6 also illustrates a top plan view 42B of the vial 12. The vial mouth 12A may have grooves 17 for needle base engagement around the base of the outside of the vial mouth 12A. These grooves are intended to snap the needle base in position on the vial mouth 12A when pressed and then removed when pulled with a slight force.

The grooves 17 on the vial mouth 12A may be in addition to grooves 16A and 16B on each side of the vial 12. The grooves 16A and 16B may also have a lock mechanism to mount the needle on the medicine vial 12. The primary purpose of grooves 16 is to slide and guide the needle on to the vial mouth 12A. Both of these groove features 16A, 16B and 17 may be used to securely mount the needle onto the vial mouth 12A.

Sub-Assembly Inject Mechanism 10A

Figure 3:
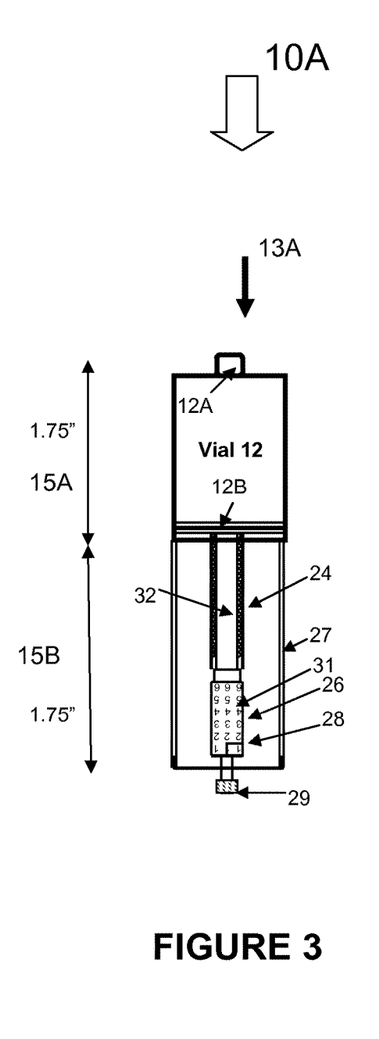
FIG. 3 is a block diagram that illustrates features of an injection mechanism of a preferred embodiment of an integrated medicine-injection device for individual use.

FIG. 3 illustrates the features of inject mechanism of sub-assembly 10A. The medicine vial 12 has a push member 12B that is coupled with a cylinder 24. A rod 32 is screwed inside the cylinder 24. The rod 32 is coupled with another cylinder member 31. The cylinder 31 has numerical markings on the surface and is coupled with a twist knob 29.

As shown in FIG. 3, the length dimension 15A of the vial is notionally 1.75 inches including the vial mouth 12A. The length dimension 15B of the inject assembly is also notionally 1.75 inches. These two dimensions combined with the length of the needle sub-assembly 10C provides for a notional dimension of 4.5 inch length of the device 10.

Figure 4:
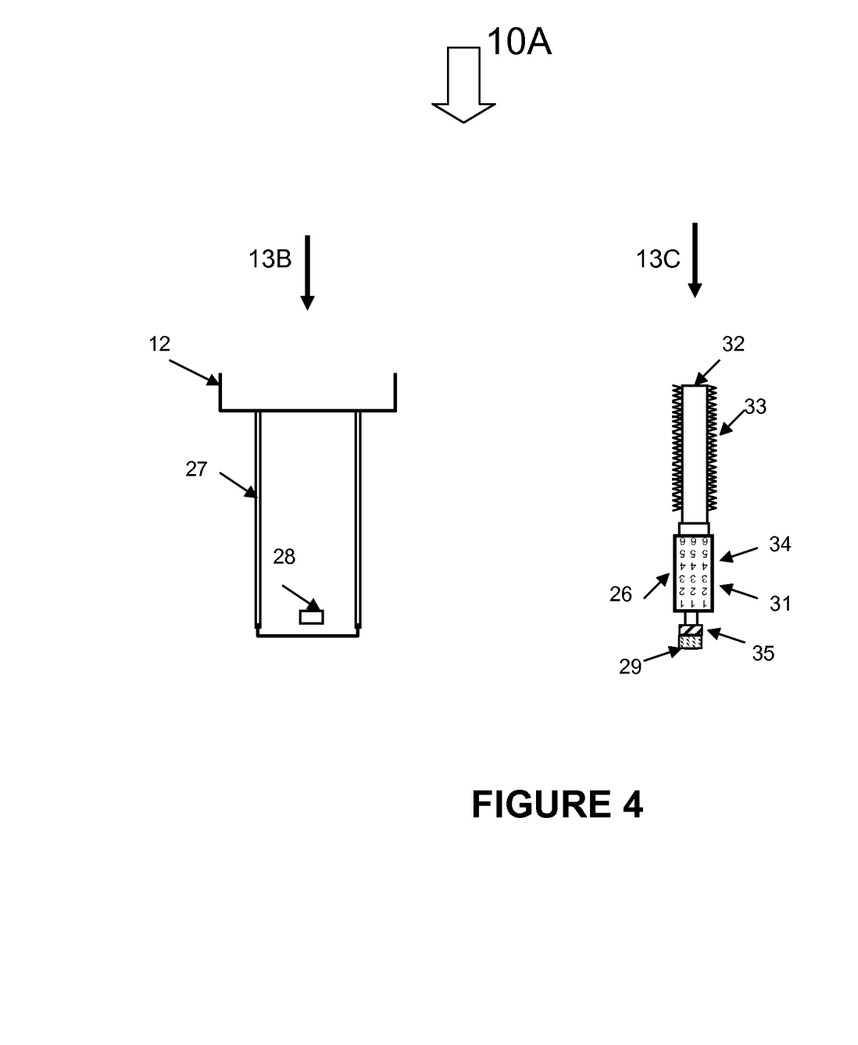
FIG. 4 is a block diagram that illustrates features of portions of an injection mechanism of a preferred embodiment of an integrated medicine-injection device for individual use.

FIG. 4 shows separate parts of the injection assembly via views 13B and 13C. With reference to view 13B, a casing 27 attached to the vial 12 covers the length of the inject mechanism and also provides for a display window 28 through which the marking related to the position of the cylinder 31, as shown in view 13C are visible. The casing cover 27 on one end is attached to the vial base 12 and on the other end has a window 28.

With reference to view 13C, the rod 32 has external threads 33 that screw the rod 32 inside the cylinder 24. The number and size of the threads are used to provide a gradation of one unit over 240 units of total movement of the cylinder 24, as in view 13A and thus to movement of the push member 12B inside the vial 12.

As a simplified illustration, the number of threads may be 80 over one inch, where rotation of the rod 32 by ⅓ of a rotation would provide for a graded movement over 240 units of the cylinder 24 and thus the push member 12B to be able to inject medicine in increments of a single unit.

As in view 13C, a spring loaded mechanism 35 lets the knob 29 be rotated freely to adjust and select a quantity of medicine to be injected, but when the knob 29 is pushed and the spring is engaged to dispense the medicine out of the vial 12, the knob is prevented from rotation.

Figure 5A:
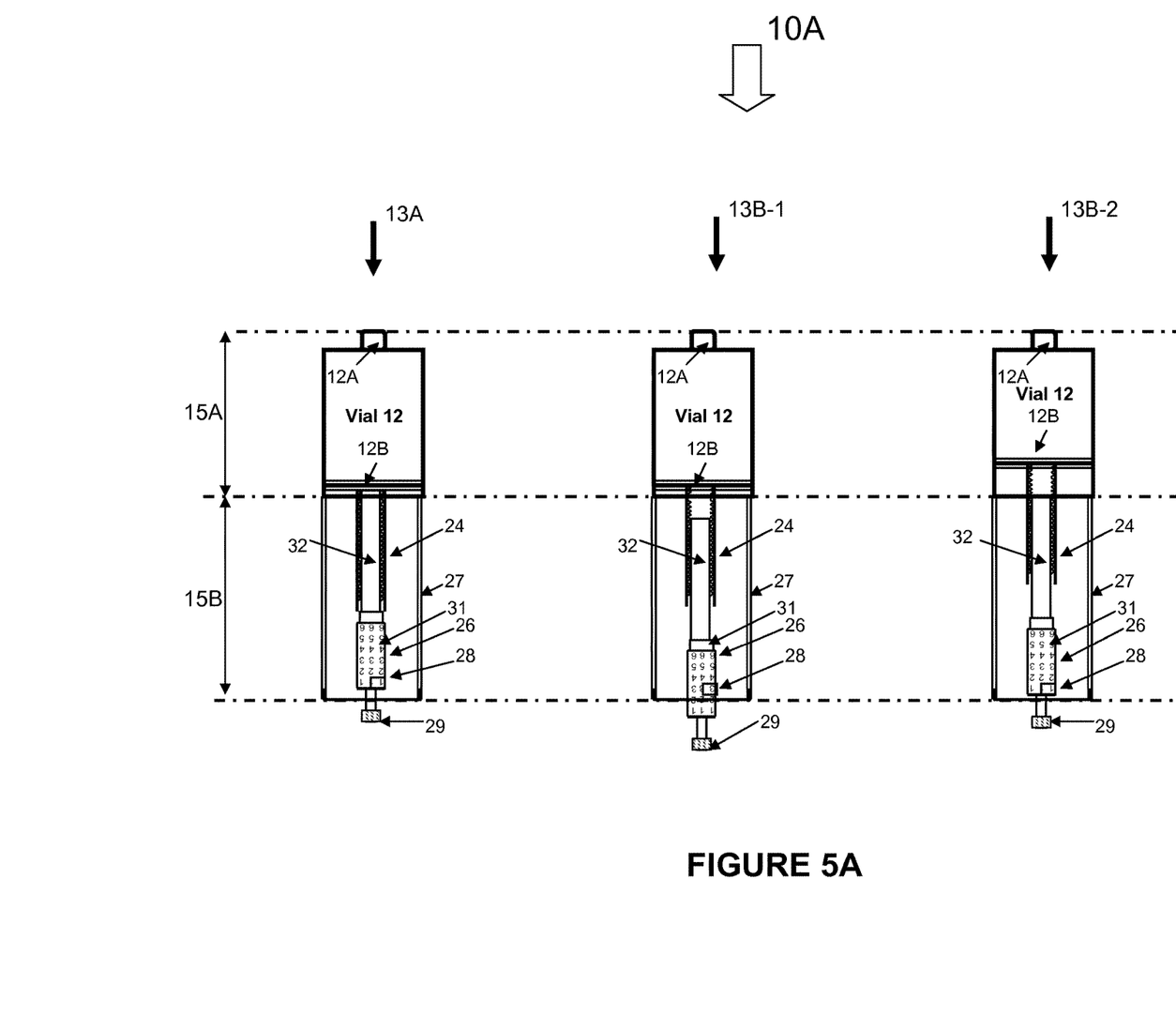
FIGS. 5A and 5B are block diagrams that illustrate operation of an injection mechanism of a preferred embodiment of an integrated medicine-injection device for individual use.
Figure 5B:
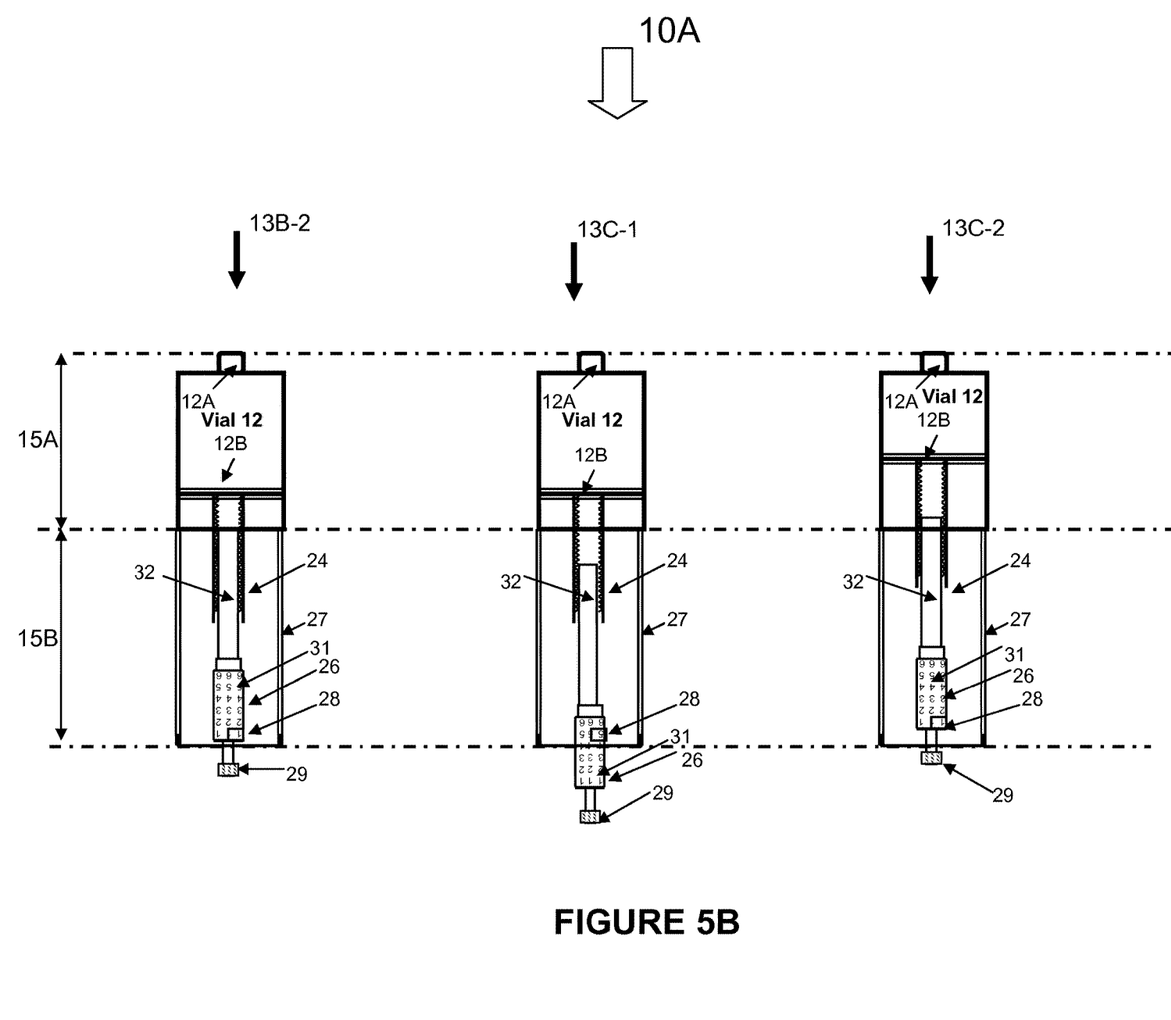

The operation of the inject mechanism 10A is illustrated with the help of FIGS. 5A and 5B. View 13A shows the mechanism and the vial before any medicine has been drawn from the vial.

As illustrated in view 13A, in the operation of the inject mechanism, the rod 32 coupled with the cylinder 31 and knob 29 when turned anti-clockwise using knob 29, unthreads the thread inside the cylinder 24 and as the rod 32 is unthreaded the knob 29 moves out as illustrated in view 13B-1. A different part of the cylinder 31 with its corresponding number 3 is visible through the display window 28 signifying that the inject mechanism can push 3 units of the medicine in the vial.

As illustrated in view 13B-2, when the knob 29 is pushed, the push member 12B through the cylinder 24 moves up inside the vial 12 pushing the medicine out of the vial 12 via the needle when one is attached to the vial mouth 12B. When the knob 29 has been pushed down, the numbers on the cylinder 31 again display an initial value through the display window 28.

When the knob 29 is pushed, it is necessary that the knob 29 does not rotate. Therefore to stop the rotation of the knob 29 when the knob 29 is pushed, a spring loaded mechanism 35 may be used in the knob 29. The spring loaded mechanism 35 lets the knob be rotated freely to adjust and select a quantity of medicine to be injected, but when the knob 29 is pushed and the spring is engaged to dispense the medicine out of the vial 12, the knob is prevented from rotation.

A similar operation as had been illustrated with the help of FIG. 5A is also illustrated with the help of FIG. 5B. View 13B-2 has been copied here for reference. View 13C-1 shows that from the prior position as in view 13B-2, the knob 29 is unscrewed further out to display a unit 5 in the display window 28. In view 13C-2 as shown when the knob 29 is pushed all the way in, the cylinder 24 moves further inside the via 12 to inject 5 units of the medicine. In view 13C-2, when the knob 29 has been pushed in, the display window 28 again shows an initial value on the cylinder 31.

It is believed that this operation of the inject mechanism is similar in many aspects to what prior art teaches except the inject mechanism is coupled to and operative with the rectangular profile medicine vial 12 and the inject mechanism casing 27 also has a rectangular profile to match the profile of the medicine vial 12.

Further, the rod 32 with external threads being positioned inside cylinder 24 with internal threads reduce the length profile of the inject mechanism. Thus FIGS. 3, 4, 5A and 5B have illustrated the injection sub-assembly 10A that is coupled with the medicine via 12 and thus integrated with the medicine vial sub-assembly 10B.

Sub-Assembly Needle Mechanism 10C

The needle assembly and mechanism 100 is illustrated with reference to FIG. 7, FIG. 8, and FIG. 9.

With reference to FIG. 7, in view 14A, a prior art needle adapted to a needle engagement mechanism 44 is shown. As illustrated in view 14A, the needle engagement mechanism 44 preferably has an apron 49. The apron 49 is in the form of a sheath or cover with a rectangular cross section. The apron 49 slides up and down as the needle engagement mechanism 44 is slid or moved up and down to mount and dismount the needle from the medicine vial mouth 12A. The apron 49 thus covers the top part of the medicine vial 12 including he vial mouth 12A and the needle base 46.

View 14B illustrates different parts of the needle engagement mechanism 44. As illustrated in view 14B, a prior art needle 22 has a needle 22A and a needle base 22B.

As illustrated in view 14B, the engagement mechanism 44 has support members 46 holding the needle base 22B. As illustrated in view 14C, these support members 46 are positioned on top of the vial 12 around the vial mouth 12A. The mechanism 44 also has engagement members 16. The support members 46 are attached to engagement members 16. The members 16 slide over the sides of the vial 12 inside the grooves 16A and 16B.

The support members 46 also have a pair of groove mechanism members 48A and 48B on the top part of the support members 46 and are used to attach to and hold a needle storage mechanism 52. The needle storage mechanism 52 is illustrated later with the help of FIG. 8.

As shown in view 14C, the needle mechanism 44 is aligned on top of the vial 12 so that when the two are mated, the grooves 16A and 16B on the two sides of the vial 12 can engage with engagement members 16 and at the same time the needle 22 base 22B can be mounted on to the vial mouth 12A.

As illustrated in view 14B, a mechanism 50 with balls on the ends of each of the engagement members 16 is seated in corresponding indentations in grooves 16A and 16B on the two sides of the vial 12 as illustrated in view 14C.

Figure 8:
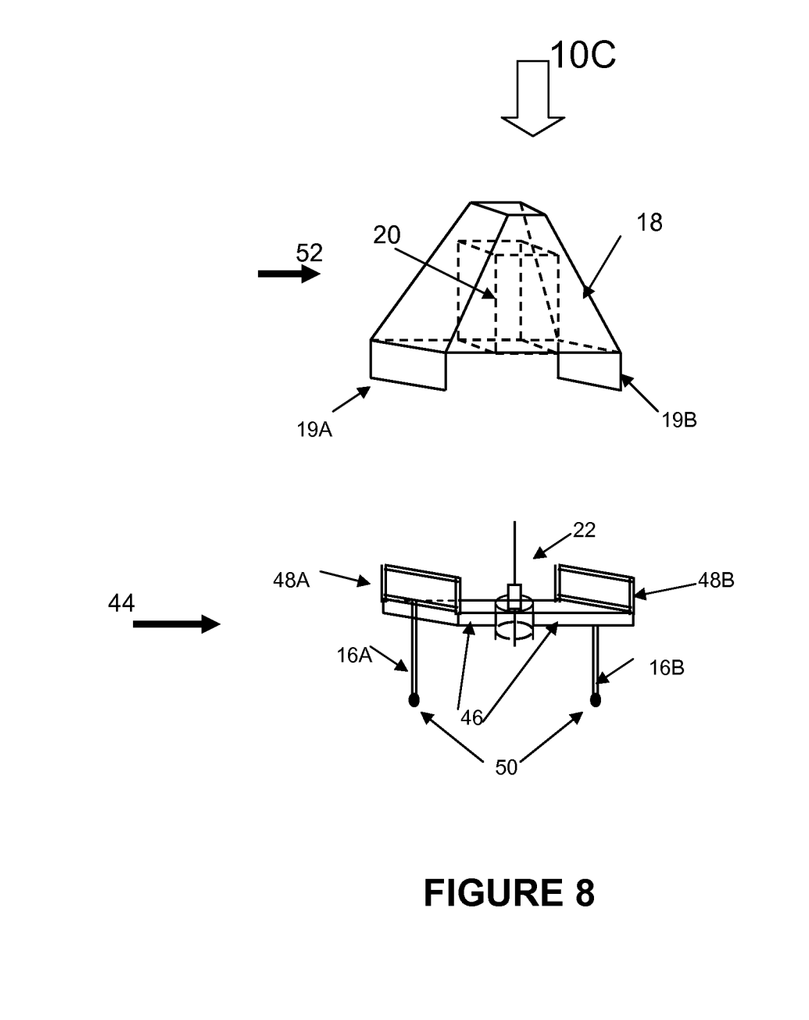
FIG. 8 is a block diagram that illustrates features of an injection needle and its storage mechanism and its associated mechanism for mounting on a medicine vial of a preferred embodiment of an integrated medicine-injection device for individual use.

As illustrated in FIG. 8, the needle storage mechanism 52 has a needle cover 18 and a needle-storage-medium 20 positioned inside the needle cover 18. The needle storage medium 20 stores the needle in-between-use and disinfects, lubricates and sanitizes the needle for each reuse. The needle cover 18 has vertical members 19A and 19B that are received in the grooves 48A and 48B of the needle engagement mechanism 44 when the needle cover 18 is pushed on the needle support mechanism 46. FIG. 9 illustrates the operation of the needle assembly 10C. The needle cover comprises a first stack as a wicking medium to absorb excess fluid droplets, a second stack as a disinfecting agent to disinfect the needle, and a third stack as a lubricating agent to lubricate the needle. The wicking medium, the disinfecting agent, and the lubricating agent are positioned inside the needle cover and are stacked on top of each other in heights for different needle lengths.

Figure 9:
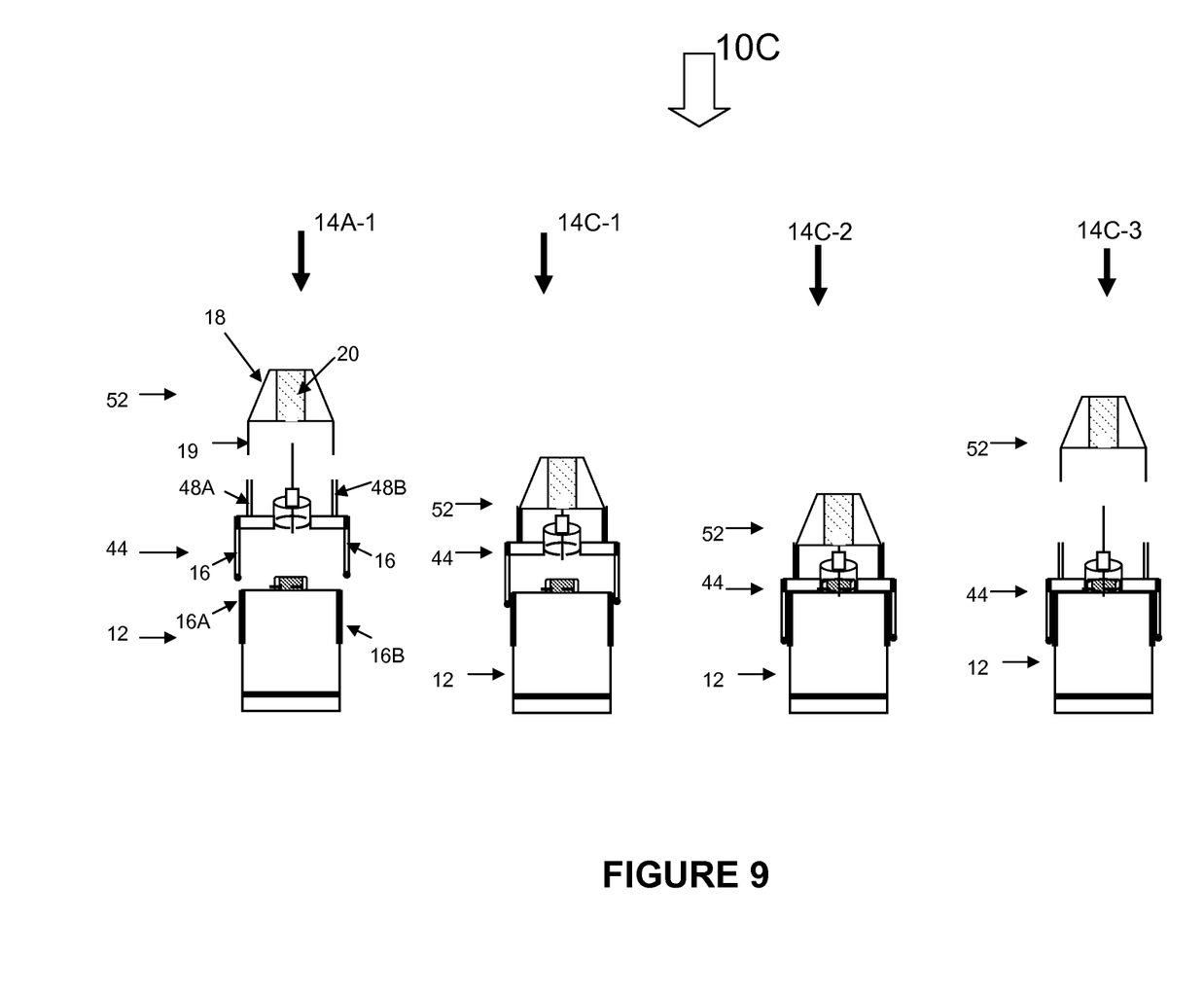
FIG. 9 is a block diagram that illustrates operational features of an injection needle and its storage mechanism and its associated mechanism for mounting on a medicine vial of a preferred embodiment of an integrated medicine-injection device for individual use.
Figure 10:
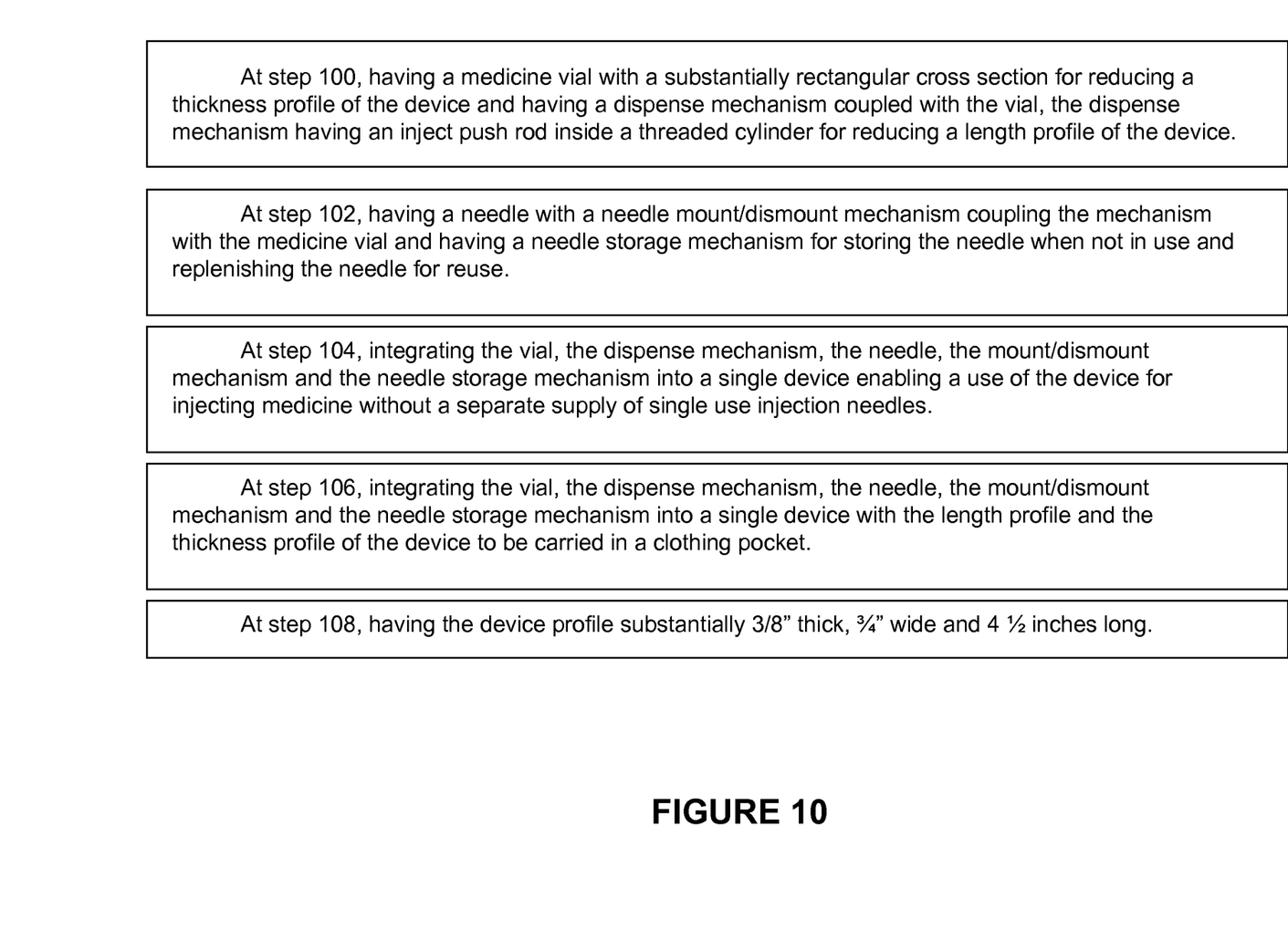
FIG. 10 is a method diagram that illustrates features of a preferred embodiment of an integrated medicine-injection device for individual use.

As illustrated in FIG. 9, in view 14A-1, the vial 12, the needle engagement mechanism 44 and the needle storage mechanism 52 are shown separately positioned on tip of each other in the order in which they are stacked.

In view 14C-1, the needle holding mechanism 44 has been engaged with the needle storage mechanism 52 via the grooves 48A and 48B. Then these two mechanisms 44 and 52 are slid over on the sides of the vial 12 with the help of engagement members 16. The engagement members 16 slide into the groves 16A and 16B on the sides of the vial 12. As illustrated in view 14C-2, the needle mount mechanism 44, and the needle storage mechanism 52 are engaged with the medicine via 12.

In view 14C-3, the needle storage mechanism 52 has been pulled away or removed exposing the needle 22 for use while the needle base 22B is mounted on to the vial mouth 12A with the needle engagement mechanism 44.

In operation these three individual mechanisms work together, starting with (i) view 14C-1 to store the needle inside the storage mechanism and not engaged with the vial 12, (ii) view 14C-2, where the needle is engaged with the vial 12, and (iii) in view 14C-3, where the needle storage cover 18 with the needle storage medium 20 has been removed exposing the needle for injection.

A portable handheld fluid-medicine-injection device for home users, has an inject mechanism sub-assembly, a medicine vial sub-assembly, a needle mount and dismount sub-assembly for the medicine vial, and a needle storage assembly for a reusable injection needle. These sub-assemblies are integrated as one device, thereby making the device convenient to carry and use.

The medicine vial has a substantially rectangular cross section along with the dispense mechanism that is coupled with the vial that minimizes a thickness profile of the device.

The inject mechanism has an inject push rod inside a threaded cylinder that minimizes a length profile of the device.

The needle mount/dismount mechanism is coupled with the medicine vial and a needle storage mechanism that stores the needle when not in use and replenishes the needle for reuse.

The vial, the dispense mechanism, the needle, the mount/dismount mechanism and the needle storage mechanism are integrated into a single device and enables the use of the device for injecting medicine without a separate supply of single use injection needles.

The vial, the dispense mechanism, the needle, the mount/dismount mechanism, and the needle storage mechanism are integrated into a single device with the length profile and the thickness profile of the device to be carried in a pocket.

The device profile is substantially ⅜" thick. The device profile is substantially ¾" wide. The device profile is substantially 4½ inches long. The device profile is substantially ⅜" thick, ¾" wide and 4½ inches long.

A portable handheld fluid-medicine-injection device for individual users, has a medicine vial with a dispense mechanism; a needle with a needle mount/dismount mechanism coupled with the medicine vial; a needle storage mechanism that stores the needle when not in use and replenishes the needle for reuse; and the vial, the dispense mechanism, the needle, the mount/dismount mechanism and the needle storage mechanism are integrated into a single device and enables the use of the device for injecting medicine without a separate supply of single use injection needles.

The medicine vial has a substantially rectangular cross section that reduces a thickness profile of the device and a dispense mechanism coupled with the vial. The dispense mechanism has an inject push rod inside a threaded cylinder that reduces the length profile of the device.

The needle storage mechanism stores the needle when not in use and replenishes the needle for reuse and has a needle storage medium with needle sanitizing agents.

A method for portable handheld fluid-medicine-injection device for home users, has the steps of, where all the steps may not be used or used in the order specified:

a. having a medicine vial with a substantially rectangular cross section for reducing a thickness profile of the device and having a dispense mechanism coupled with the vial, the dispense mechanism having an inject push rod inside a threaded cylinder for reducing the length profile of the device;

b. having a needle with a needle mount/dismount mechanism coupling with the medicine vial and having a needle storage mechanism for storing the needle when not in use and replenishing the needle for reuse;

c. integrating the vial, the dispense mechanism, the needle, the mount/dismount mechanism and the needle storage mechanism into a single device enabling a use of the device for injecting medicine without a separate supply of single use injection needles;

d. integrating the vial, the dispense mechanism, the needle, the mount/dismount mechanism and the needle storage mechanism into a single device with the length profile and the thickness profile of the device to be carried in a pocket;

f. having the device profile substantially ⅜" thick, ¾" wide and 4½ inches long.

Mode of Use

A preferred mode of use of device 10 is described here while other modes of use are not ruled out. When a need arises to inject insulin, based on glucose reading or at meal time, a user would retrieve device 10 from their pocket or pocketbook. User would decide how many units to inject and would dial up that quantity using knob 29 and see the quantity that has been dialed in the window 28.

The user would then grip the apron 49 with thumb and forefinger and slide down the apron 49 to mount the needle base 22B via the needle engagement mechanism 44 on to the medicine vial mouth 12A. In this position the needle base 22B is locked on to the vial mouth 12A with the help of grooves 17 around the vial mouth 12A. The mechanism 44 is also locked on to the vial 12 with the help of the engagement members 16 that move in grooves 16A and 16B and the indent mechanisms 50 incorporated therein.

The user then would remove the needle cover 52 from the needle engagement mechanism 44 to expose the needle 22. The user would then insert the needle 22 in the tissue and depress knob 29. After the injection process is completed, user would remove the needle 22 from the tissue.

The user then would hold the apron 49 and slide up the needle engagement mechanism 44 to dismount the needle base 22B from the vial mouth 12B. This would also unlock the indent mechanism 50 on the vial 12 and relock it on the top part of the vial 12.

The user then would mount the needle cover mechanism 52 back on to the needle 22 with the help of the guides 19A and 19B on the mechanism 52 and grooves 48A and 48B on the needle engagement mechanism 44.

As soon as the needle cover 52 is slid back over the needle 22 with the help of guides 19A and 19B, the process of sanitizing, disinfecting and lubricating the needle 22 with the help of needle storage medium 20 for the next use has begun. Then the user would put the device 10 back in the pocket until next use.

When the medicine in the vial 12 is used up, the device 10 would be disposed of. It is assumed that given the quantity of medicine in the vial 12, the device 10 would last from a week to ten days, assuming 25 to 30 or so units are injected everyday. The device would last more or less than this time depending upon quantity of medicine needed by a given user.

Based on the number of days of ten the device 10 would last, and the number of times the device 10 is used in a day, which is assumed to be three times, the needle 22 of the device 10 would be reused approximately 30 times. The needle storage medium 20 is sized to be able to replenish the needle 22 at least these number of times, as the device 10 is discarded after that many number of uses.

Method of Operation

As illustrated in FIG. 10, method for using the device 10 has the following steps where all the steps may not be used or used in the order specified:

At step 100, having a medicine vial with a substantially rectangular cross section for reducing a thickness profile of the device and having a dispense mechanism coupled with the vial, the dispense mechanism having an inject push rod inside a threaded cylinder for reducing the length profile of the device.

At step 102, having a needle with a needle mount/dismount mechanism coupling the mechanism with the medicine vial and having a needle storage mechanism for storing the needle when not in use and replenishing the needle for reuse.

At step 104, integrating the vial, the dispense mechanism, the needle, the mount/dismount mechanism and the needle storage mechanism into a single device enabling a use of the device for injecting medicine without a separate supply of single use injection needles.

At step 106, integrating the vial, the dispense mechanism, the needle, the mount/dismount mechanism and the needle storage mechanism into a single device with the length profile and the thickness profile of the device to be carried in a clothing pocket.

At step 108, having the device profile substantially ⅜" thick, ¾" wide and 4½ inches long.

In summary, the preferred embodiments are a portable handheld fluid-medicine-injection device for individual users, has a medicine vial has a substantially rectangular cross section that reduces a thickness profile of the device and a dispense mechanism coupled with the vial, the dispense mechanism has an inject push rod inside a threaded cylinder that reduces a length profile of the device. The device has a needle with a needle mount/dismount mechanism coupled with the medicine vial and a needle storage mechanism that stores the needle when not in use and replenishes the needle for reuse.

While the particular invention, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

The invention claimed is:

1. A portable handheld fluid-medicine-injection device for home users, comprising:
    an insulin pen, wherein the insulin pen uses exclusively a pen needle and the insulin pen further comprising a first assembly comprising an inject mechanism sub-assembly, and a medicine vial sub-assembly with a medicine vial;
    a second assembly, physically separate from the first assembly, comprising a pen needle mount and dismount sub-assembly for mounting and dismounting the pen needle to a dispense end of the medicine vial, wherein the pen needle mount and dismount sub-assembly has a slide mechanism and a guide mechanism for mounting and dismounting the pen needle on the dispense end of the medicine vial;
    the guide mechanism has guide members positioned both on the slide mechanism and the medicine vial, wherein the slide mechanism along with the guide mechanism is used for mounting and dismounting the pen needle onto and from the medicine vial;
    the slide mechanism and the guide mechanism dismount the pen into a position wherein the pen needle is not in fluid communication with the medicine vial, and wherein the pen needle mount and dismount sub-assembly still remains engaged with the medicine vial sub-assembly;
    a pen needle storage assembly configured for storing the pen needle in a dismount position on the slide mechanism, wherein the pen needle storage assembly has a needle cover with a first stack as a wicking medium to absorb excess fluid droplets, a second stack as a disinfecting agent to disinfect the pen needle, and a third stack as a lubricating agent to lubricate the pen needle that are positioned inside the needle cover, wherein the wicking medium, the disinfecting agent, and the lubricating agent are stacked on top of each other in heights for different needle lengths, and wherein the pen needle storage assembly is integrated with the slide mechanism of the pen needle mount and dismount sub-assembly as a single integrated assembly enabling the pen needle to be prepared for reuse inside the needle cover when the single integrated assembly is dismounted from the medicine vial.

2. The portable handheld fluid-medicine-injection device as in claim 1, further comprising:
    the portable handheld fluid-medicine-injection device, including its subassemblies and the pen needle storage assembly has a substantially rectangular cross section for a thickness profile of the portable handheld fluid-medicine-injection device.

3. The portable handheld fluid-medicine-injection device as in claim 2, comprising:
the portable handheld fluid-medicine-injection device, including its subassemblies and the pen needle storage assembly are integrated into a single device with a length profile and the thickness profile of the portable handheld fluid-medicine-injection device to be carried in a pocket.

4. The portable handheld fluid-medicine-injection device as in claim 2, comprising:
the thickness profile of the portable handheld fluid-medicine-injection device is substantially ⅜" thick.

5. The portable handheld fluid-medicine-injection device as in claim 2, comprising:
the thickness profile of the portable handheld fluid-medicine-injection device is substantially ¾" wide.

6. The portable handheld fluid-medicine-injection device as in claim 2, comprising:
a length profile of the portable handheld fluid-medicine-injection device is substantially 4½ inches long.

7. The portable handheld fluid-medicine-injection device as in claim 2, comprising:
the portable handheld fluid-medicine-injection device is substantially ⅜" thick, ¾" wide and 4½ inches long.

8. The portable handheld fluid-medicine-injection device. as in claim 1, further comprising:
the inject mechanism sub-assembly has an inject push rod with outer threads inside an inner threaded cylinder for a length profile of the portable handheld fluid-medicine-injection device.

9. The portable handheld fluid-medicine-injection device as in claim 1, further comprising:
the pen needle mount and dismount sub-assembly is coupled with the medicine vial subassembly; and the pen needle storage assembly that stores the pen needle when not in use for reuse.

10. The portable handheld fluid-medicine-injection device as in claim 1, further comprising:
the portable handheld fluid-medicine-injection device, including its subassemblies and the pen needle storage assembly are integrated into a single device and enables a use of the portable handheld fluid-medicine-injection device for injecting medicine without a separate supply of single use injection needles.

11. A method for portable handheld fluid-medicine-injection device for home users, comprising the steps of:
providing an insulin pen, wherein the insulin pen uses exclusively a pen needle and the insulin pen further comprising a first assembly comprising an inject mechanism sub-assembly, and a medicine vial sub-assembly with a medicine vial;
providing a second assembly, physically separate from the first assembly, comprising a pen needle mount and dismount sub-assembly for mounting and dismounting the pen needle to a dispense end of the medicine vial, wherein the pen needle mount and dismount sub-assembly has a slide mechanism and a guide mechanism for mounting and dismounting the pen needle onto and from the dispense end of the medicine vial;
positioning in the guide mechanism guide members both on the slide mechanism and the medicine vial, wherein the slide mechanism along with the guide mechanism is used for dismounting the pen needle from the medicine vial;
dismounting by the slide mechanism and the guide mechanism the pen needle into a position wherein the pen needle is not in fluid communication with the medicine vial, and wherein the pen needle mount and dismount sub-assembly still remains engaged with the medicine vial sub-assembly;
providing a pen needle storage assembly configured for storing the pen needle in a dismount position on the slide mechanism, wherein the pen needle storage assembly has a needle cover with a first stack as a wicking medium to absorb excess fluid droplets, a second stack as a disinfecting agent to disinfect the pen needle, and a third stack as a lubricating agent to lubricate the pen needle that are positioned inside the needle cover, wherein the wicking medium, the disinfecting agent, and the lubricating agent are stacked on top of each other in heights for different needle lengths, and wherein the pen needle storage assembly is integrated with the slide mechanism of the pen needle mount and dismount sub-assembly is integrated with the slide mechanism of the needle mount and dismount assembly as a single integrated assembly enabling the pen needle to be prepared for reuse inside the needle cover when the single integrated assembly is dismounted from the medicine vial.

12. The method as in claim 11, further comprising the steps of:
coupling the pen needle mount and dismount sub-assembly with the medicine vial sub-assembly; and the pen needle storage assembly that stores the pen needle when not in use for reuse.

13. The method as in claim 11, further comprising the steps of:
integrating the inject mechanism sub-assembly, the medicine vial sub-assembly, the pen needle mount and dismount sub-assembly for mounting and dismounting the pen needle to the dispense end of the medicine vial sub-assembly, and the pen needle storage assembly for a reusable pen needle, into a single device enabling a use of the portable handheld fluid-medicine-injection device for injecting medicine without a separate supply of single use injection needles.

14. The method as in claim 11, comprising the steps of:
integrating the portable handheld fluid-medicine-injection device, including its assemblies and the pen needle storage assembly into a single device with a length profile and a thickness profile of the portable handheld fluid-medicine-injection device for carrying in a pocket.

15. The method as in claim 14, comprising the steps of:
having the thickness profile of the portable handheld fluid-medicine-injection device substantially ⅜" by ¾" and the length profile substantially 4½ inches long.

16. A portable handheld fluid-medicine-injection device for individual uses, comprising:
a pen injection needle;
a medicine vial with a dispense mechanism;
a needle mount/dismount mechanism coupled with the medicine vial, wherein the needle mount/dismount mechanism has a slide mechanism and a guide mechanism, where positioning in the guide mechanism guide members both on the slide mechanism and the medicine vial, wherein the slide mechanism along with the guide mechanism is used for mounting and dismounting the pen injection needle on to and from the medicine vial;

the slide mechanism and the guide mechanism dismount the pen injection needle into a position where the pen injection needle is not in fluid communication with the medicine vial, and wherein the needle mount/dismount mechanism still remains engaged with the medicine vial;

A needle storage mechanism comprising a needle cover with a first stack as a wicking medium to absorb excess fluid droplets, a second stack as a disinfecting agent to disinfect the pen injection needle, and a third stack as a lubricating agent to lubricate the pen injection needle for reuse, when stores in the needle storage mechanism, wherein the wicking medium, the disinfecting agent, and the lubricating agent are positioned inside the needle cover and are stacked on top of each other in heights for different needle lengths;

the needle mount/dismount mechanism and the needle storage mechanism store the pen injection needle detached from the medicine vial, and wherein the needle storage mechanism is integrated with the needle mount/dismount mechanism as a single integrated assembly enable the pen injection needle to be prepared for reuse inside the needle cover when the single integrated assembly is dismounted from the medicine vial.

17. The portable handheld fluid-medicine-injection device as in claim 16, comprising:

the medicine vial has a substantially rectangular cross section that reduces a thickness profile of the portable handheld fluid-medicine-injection device and the dispense mechanism coupled with the medicine vial, the dispense mechanism has an inject push rod inside a threaded cylinder that reduces a length profile of the portable handheld fluid-medicine-injection device.

\* \* \* \* \*